United States Patent [19]

Christiansen

[11] Patent Number: 4,537,080
[45] Date of Patent: Aug. 27, 1985

[54] SIDE LOADING SPECIMEN GRIP

[75] Inventor: John A. Christiansen, Minneapolis, Minn.

[73] Assignee: MTS Systems Corporation, Eden Prairie, Minn.

[21] Appl. No.: 585,354

[22] Filed: Mar. 1, 1984

Related U.S. Application Data

[63] Continuation-in-part of Ser. No. 350,056, Feb. 18, 1982, abandoned.

[51] Int. Cl.³ .............................................. G01N 3/04
[52] U.S. Cl. ........................................ 73/857; 73/859
[58] Field of Search .......................... 73/857, 859, 860

[56] References Cited

U.S. PATENT DOCUMENTS

| | | | |
|---|---|---|---|
| 3,224,259 | 1/1962 | De Nicola | 73/103 |
| 3,320,798 | 5/1967 | Gram | 73/103 |
| 3,335,603 | 8/1967 | Gram | 73/103 |
| 3,498,121 | 3/1970 | Engelbrecht et al. | 73/103 |

FOREIGN PATENT DOCUMENTS 2028030  6/1970  Fed. Rep. of Germany .

OTHER PUBLICATIONS

MTS Product Specification Sheet, Series 642.1X Flat Plate Grips.
MTS Product Specification Sheet, Models 644.35 and 644.36 Cast Metal Grips.
MTS Product Specification Sheet, Series 645 Tension Grips.
MTS Product Specification Sheet, Serial 640.1X Clevis Pin Grips.

Primary Examiner—Anthony V. Ciarlante
Attorney, Agent, or Firm—Kinney & Lange

[57] ABSTRACT

Hydraulically actuated grips are constructed to permit loading of specimens from either side of the grips. The grips are particularly adapted for use with flat specimens, are easily actuated, and are symmetrically designed so that when actuated, the grips do not exert any substantial axial load on the specimen and a uniform clamping force is applied laterally across the specimen. In addition, the grips, which can be used for either tensile or compressive loading, do not exert any bending moment on the specimen during test loading.

12 Claims, 7 Drawing Figures

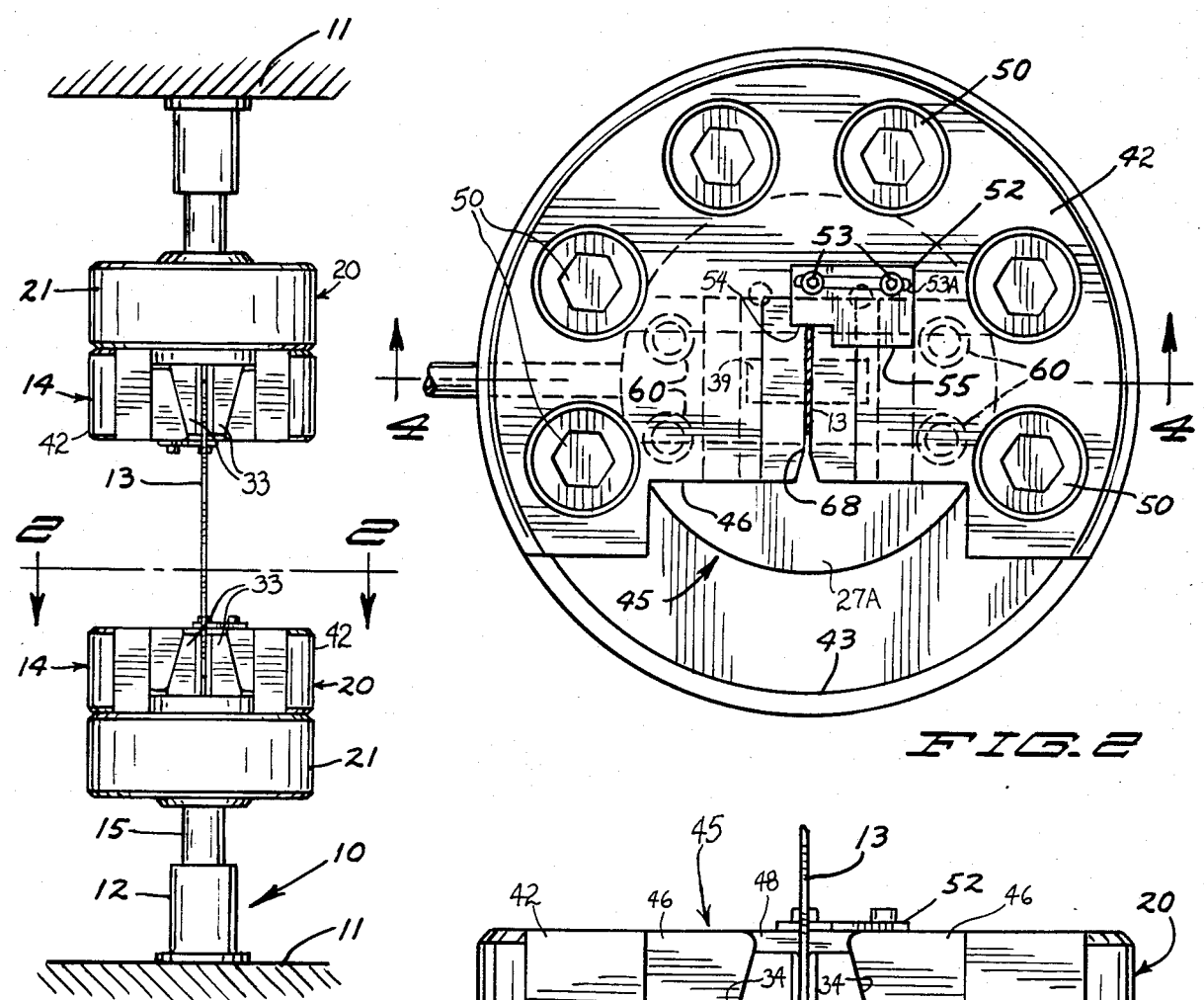
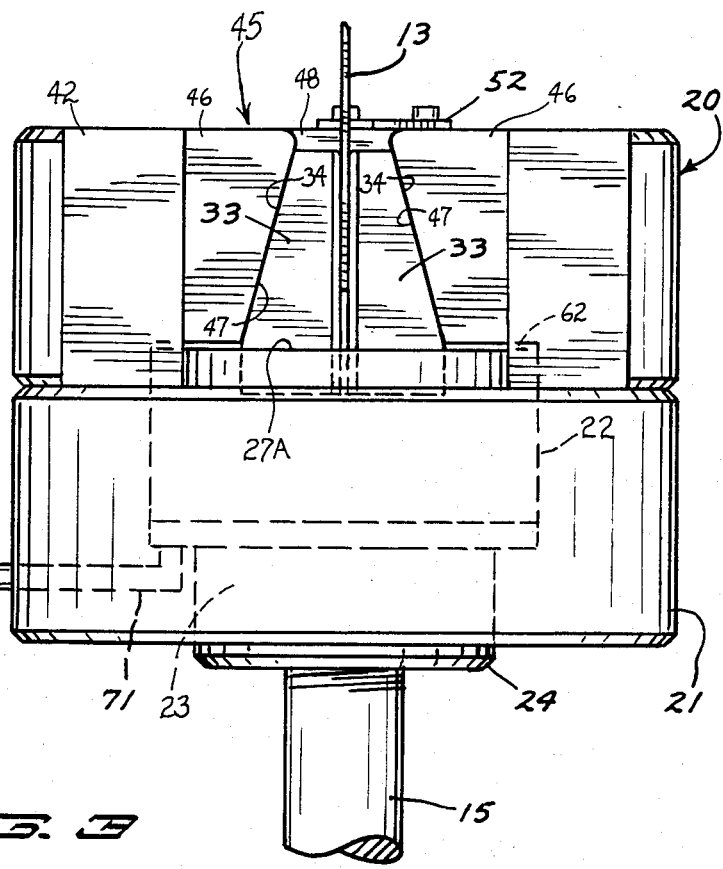

SIDE LOADING SPECIMEN GRIP

This is a continuation-in-part of Ser. No. 350,056 filed Feb. 18, 1982 now abandoned.

BACKGROUND OF THE INVENTION

1. Field of the Invention

The present invention relates to side loading specimen grips that are hydraulically actuated without causing any substantial movement of the specimen during clamping and which eliminates undesirable bending moments during specimen testing.

2. Description of the Prior Art.

In the prior art, various specimen grips have been advanced. Self aligning and hydraulically actuated grips are shown in U.S. Pat No. 3,335,603 issued to Martin M. Gram, on Aug. 15, 1967. In this patent the actuator cam for the grips is a cylindrical member and the specimen was to be installed from the end of the grip. Additionally, this patent shows a self aligning head connection to the actuator exerting the load on the specimen.

U.S. Pat No. 3,224,259 shows a typical side loading mechanically actuated grip for tensile testing only, wherein there is longitudinal motion of the jaws relative to the grip during tension testing of the specimen. A specimen can be loaded into this mechanical grip from a front side only—the grip has a back portion connecting its two side grip pieces. Thus, as the grip is actuated, the grip force is uneven across the specimen from front to back because the side grip pieces which act on the specimen grip jaws act as cantilevers. The clamping force on the specimen is greater adjacent the back of the grip than near the front. This uneven force or distortion of the clamping force can place a bending moment on the specimen and thereby influence the specimen test results, especially with a specimen of relatively brittle material. The present device permits side loading of a specimen, and in particular flat plate-like specimens, and has actuated jaws that move only transverse to the longitudinal axis of the specimen, thereby substantially eliminating any induced load along the longitudinal axis of the specimen. The present device minimizes premature specimen loading, which, if of significant magnitude, could cause the specimen to yield or fail during gripping. In addition, the present device is generally symmetrical to eliminate front-to-back gripping force differentials across the grip jaws. This prevents any bending moment from being applied to the specimen and thus provides more accurate test results. Specimen grips of the present invention offer the further advantages of faster testing and processing time, since neither of the grips needs to be moved longitudinally along the specimen test axis in order to install a specimen. While a greater rate of specimen testing is possible with the specimen grips of the present invention, safety is not compromised for speed. The specimen grips of the present invention are safer than prior art grips because once set up for a particular size specimen, there is no need to move the grips longitudinally in order to place the specimen within the grips for testing. An operator simply slides the specimen from the side in between the grip jaws of the specimen grips and the grips are actuated to clamp specimen.

The assignee of the present application has sold grips such as those shown in U.S. Pat. No. 3,335,603, as Model Series 641 Hydraulically Operated Grips. These grips show horizontal or transverse gripping motion but the outer housing completely encloses the wedge arrangement, and they do not permit loading of specimens from the side. Additionally, said assignee has sold "Series 645 Mechanical Wedge Grips" for tension loading. These are mechanically actuated grips into which a specimen may be installed from one side only, and the wedges used for these grips tend to move vertically as they are locked onto the specimen. Another specimen testing grip is shown in U.S. Pat. No. 3,320,798, issued to Martin M. Gram, on May 23, 1967.

SUMMARY OF THE INVENTION

A side loading specimen grip suitable for use in both tensile and compressive loading of specimen is hydraulically actuated and permits clamping the specimen in place with movement of the clamping jaws only transverse to the longitudinal axis of the specimen to be loaded so that axial loading of the specimen during the clamping is virtually eliminated. Further, the specimen clamping force is achieved hydraulically with a sufficient load so that the grip and specimen assembly is preloaded above the maximum load applied to the specimen during testing so that there is no further flexing or movement of the jaws during the testing cycle. This will enhance system control thereby improving the testing results. The hydraulically achieved preload gives the grip the capability to run to it's maximum capacity in both specimen tensile and compressive loading without loss in continuity of the grip and specimen assembly.

The housing for actuating the jaws is securely mounted in the clamp body of the grip, the clamping force can be made sufficient so the specimen is held without further grip movement during application of the full testing force. The housing is generally symmetrical and has a pair of opposed identical recesses therein so that specimen insertion between the two grip jaws is possible from either side of the grip jaws.

As the hydraulic preload is applied, the outer housing of the grip is moved to act on the grip jaw wedge surfaces and force the jaws simultaneously against the specimen in a direction perpendicular to the longitudinal axis of the specimen. Suitable means, such as hydraulic or mechanical bias means, are provided to cause grip jaw separation when the hydraulic pressure exerting the clamping force is released.

The grip is made so that it can be used in either tension or compression loading. Of course, the jaws of the grip are adaptable for acceptance of other specimen configurations also, such as cylindrical end specimens.

BRIEF DESCRIPTION OF THE DRAWINGS

FIG. 1 is a fragmentary schematic view of a typical testing machine in which the grip of the present invention is utilized;

FIG. 2 is a sectional view looking down on the lower grip and taken as on line 2—2 in FIG. 1;

FIG. 3 is a side view of the device of FIG. 2;

DETAILED DESCRIPTION OF THE PREFERRED EMBODIMENTS

Figure 4:
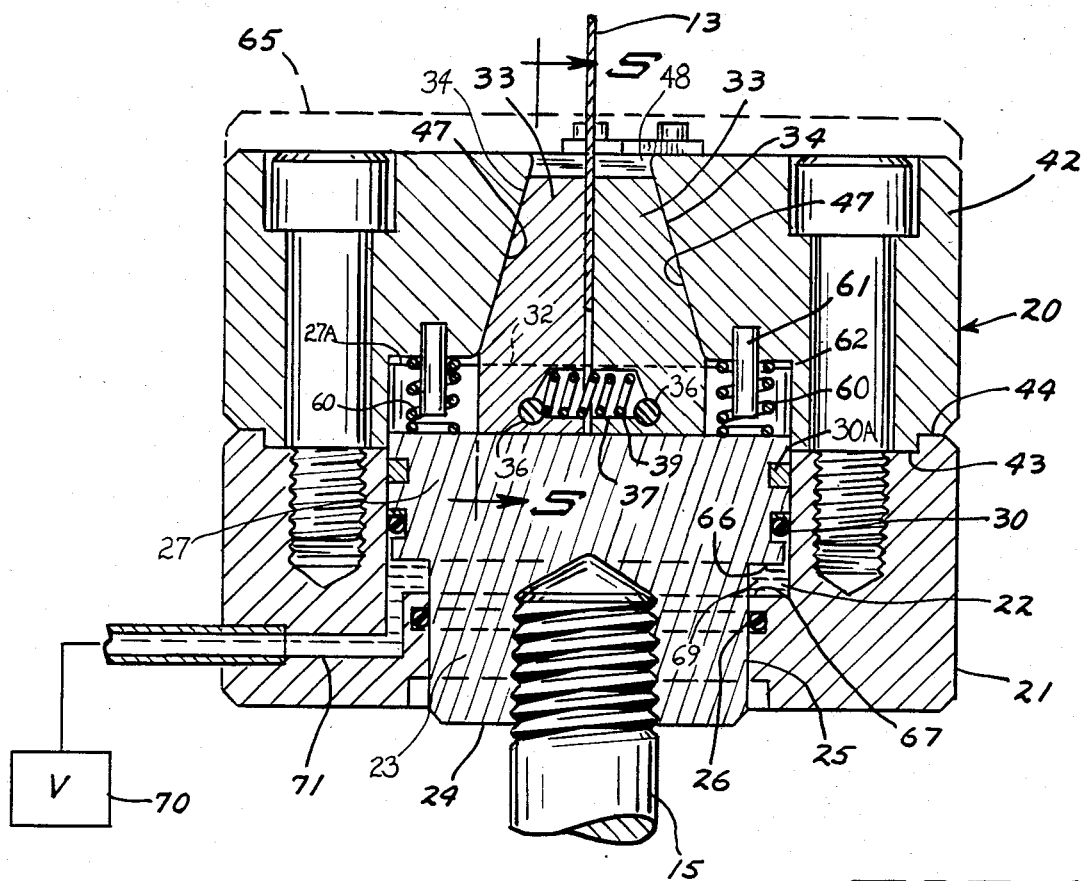
FIG. 4 is a sectional view taken as on line 4—4 in FIG. 2.

A testing machine indicated schematically at 10 includes a frame 11 which is an ordinary load frame commonly used for tensile testing of specimens, and is represented only by supports in FIG. 1. The load frame 11 includes an actuator 12 of conventional design that is used for applying either a tension load, a compression load, or an alternating tension and compression load along a longitudinal test axis of a specimen indicated at 13 that is held in a pair of grips 14,14. The grips 14 made according to the present invention are made so that the specimen 13 (shown as plate steel) can be loaded from the side of the grips 14. The upper grip 14 is attached to the load frame 11 in any suitable manner, and the lower grip 14, as will be shown, is attached to the actuator rod 15 of the actuator 12.

Referring now to FIGS. 2 through 5, each of the grips 14 is made up to be hydraulically actuated and comprises an outer grip body housing 20 that is made in two sections. The base or lower body section indicated at 21 of the grip housing 20 has an chamber or bore 22 defined therethrough which forms a hydraulic cylinder. The bore 22 has a grip jaw mounting body assembly 23 that has a neck 24 extending through a neck portion 25 of bore 22. The neck 24 in turn is attached to the hydraulic actuator rod 15, and therefore is carried by the rod 15. The neck 24 is sealed from leaking hydraulic fluid with an O-ring 26. The mounting body assembly 23 includes a piston portion 27 which fits inside the upper portion of chamber 22. The piston portion 27 is sealed with an O-ring 30, and a wiper 30A is used if desired.

Figure 5:
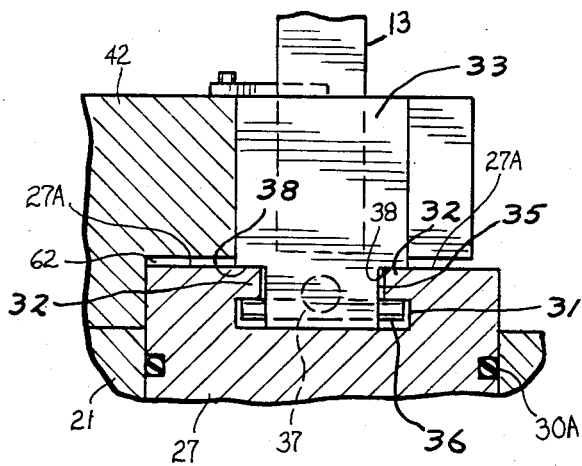
FIG. 5 is a fragmentary sectional view taken as on line 5—5 in FIG. 4.

The upper end of the grip jaw mounting body assembly 23 has a T-slot 31 defined therein, as shown in FIG. 5. The T-slot 31 is formed by a cross channel or slot having a pair of overhanging shoulders 32,32. A pair of hardened grip jaws 33 are provided, with each jaw 33 having an outer wedge surface 34 and an integral shank or tang member 35 which extends between the overhanging shoulders 32,32 and into the T-slot 31. The shank or tang member 35 of each of the grip jaws has a cross member 36 that extends under the shoulders 32 to hold the jaws 33 in place in the T-slot 31 as shown in FIG. 4. Additionally, the jaws 33 are each provided with an internal recess 37 for mounting a bias means, such as a spring 39, which loads the jaws 33 apart or tends to separate the two jaws 33. The shoulders 32 and T-slot 31 form a slide for the jaws 33 as they are actuated.

An upper surface of the mounting body assembly 23 forms an upper hardened surface 27A (the upper surfaces of shoulders 32) along the edges of the T-slot 31 and the jaws 33 have hardened overhanging surfaces 38 on opposite sides of the tang 35 which ride on the upper hardened surfaces 27A of the shoulders 32,32 so that the hardened surfaces 27A and 38 ride together when the grip 14 is actuated. The cross members 36 riding in the T-slot 31 prevents movement of grip jaws 33 upwardly with respect to the mounting body assembly 23 as viewed in FIG. 5. Thus, when the piston portion 27 of the mounting body 3 moves longitudinally along the test axis, the grip jaws 33 move simultaneously with it.

The outer grip housing 20 further includes an upper body section 42, one side of which is partially cut away, as shown in FIG. 2. The lower edge of the upper body section 42 has an annular pilot member 43 that fits inside an annular flange 44 on the lower body section 21. The flange 44 forms an annular shoulder around the lower body section 21. As can be seen in FIG. 2, the upper section 42 is cut away along one side, as shown at 45. This cut away or recess 45 forms a pair of surfaces 46 on the upper body section 42 that are substantially vertical surfaces. The surfaces 46 are on opposite sides of a pair of camming surfaces 47,47 that are formed on an internal cavity 48 of the upper body section 42. The surfaces 47 engage the wedge surfaces 34 of the jaws 33. The cavity 48, which extends to the top or upper end of the upper body section 42, is thus laterally open through the recess 45. The space between the jaws 33, which defines the opening in which a specimen 13 can be inserted, is thus accessible from the side of the grip 14 through recess 45.

The recess 45 therefore provides a direct access from the side into the grip jaws 33,33 and permits inserting a specimen 13 between the jaws 33 when the jaws 33 are separated or loosened. There is no need to move the entire grip 14 longitudinally in order to install the specimen 13.

The upper body section 42 fits securely in place with the pilot member 43 inside the flange 44. Cap screws indicated at 50 are threaded into the lower body section 21. These cap screws can provide a substantial preload of the upper body section 42 against the lower body section 21, and this will keep the body sections 21 and 42 from separating when the grip 14 is actuated.

The upper end of the upper body section 42 is used for mounting an adjustable specimen stop 52 that is held in place with a pair of cap screws 53,53. The stop 52 is adjustable by having a slot 53A in the stop 52 for the cap screws 53, so that a plurality of different positions are provided. As shown, edges 54 and 55 provide stop positions.

The grip housing 20 is urged in a direction away from the piston portion 27 of the grip jaw mounting body assembly 23 by bias means, such as four springs indicated at 60 that are held inside the T-slot 31 and passed between the shoulders 32,32. These springs 60 are held in place with dowels 61 that are fastened into the upper body section 42 and protrude downwardly into the T-slot 31. The shoulders 32 can be recessed for providing spring clearance.

Note that the upper body section 42, in addition to having the cam surfaces 47, has a bore indicated at 62 aligned with bore 22 into which the piston portion 27 of the grip jaw mounting body assembly 23 can move. Furthermore, when the grip 14 is actuated, there is clearance between the upper surface 27A and the upper end of the bore 62, as shown in FIG. 5.

FIGS. 3 and 4 show the grip 14 clamped, and thus the grip housing 20 is forced downwardly relative to the grip jaw mounting body assembly 23, so that the clearance at the top of the piston portion 27 in bore 62 is relatively small. The springs 60 urge the grip housing 20 upwardly when hydraulic pressure is released from the grip 14.

ACTUATION

When a specimen 13 is to be inserted, the springs 60, as well as the spring 39, urge the jaws 33 apart and the housing 20 upwardly as shown in dotted lines 65 in FIG. 4. This reduces the spacing between the underside 66 of the piston portion 27 and a mating surface 67 of the bore or chamber 22. The space between these surfaces in bore 22 forms the active hydraulic cylinder chamber 69 (it is an annular chamber) for actuating the grip 14.

Once the specimen 13 has been slid in between the jaw gripping surfaces indicated at 68 in FIG. 2, hydraulic pressure is supplied from a valve shown schematically at 70 through a suitable conduit indicated in dotted lines at 71 into the hydraulic cylinder chamber 69. This hydraulic pressure acts between the surfaces 66 and 67 to force the lower body section 21 downwardly relative to the grip jaw mounting body assembly 23, and of course, the cap screws 50 will carry the upper body section 42 downwardly as well. In turn, the camming surfaces 47 acting on the wedge surfaces 34 of the jaws 33 tend to move the jaws 33 horizontally toward each other. The shoulder surfaces 38 of the jaws 33 ride on the upper surface 27A of the shoulders 32 and move only horizontally (the grip jaw mounting body assembly 23 carries the jaws 33) so relative axial movement between the specimen 13 and the grip 14 is virtually eliminated. Note that the actuator rod 15 holds the grip jaw mounting body assembly 23 in its desired position during the actuation of the grip 14, which actuates the grip housing 20 to move the jaws 33 horizontally toward each other.

By using a high enough hydraulic pressure, the gripping action (and the clamping force of the jaws 33) becomes sufficiently high to preload the grips 14 to a point where there is virtually no change in grip force nor relative movement between the jaws 33 and surfaces 47 when the actuator 12 is operated for loading the specimen 13. The grip jaws 33 are pre-loaded to a point where the testing load from the actuator rod 15 is less than the force being exerted by the hydraulic fluid under pressure in the chamber 69. The load path for both tensile and compressive specimen testing is thus through the mounting body assembly 23 and grip jaws 33 to the specimen 13.

In addition, by employing a straight horizontal jaw movement, which also is defined as movement perpendicular to the longitudinal axis of the specimen, the specimen stresses are minimized during the initial gripping action. Therefore, there is virtually no axial movement of the specimen.

When the specimen 13 has been tested, either to compressive or tensile failure or the like, and the parts are to be removed from the grips 14, the pressure from valve 70 to each grip 14 is released, and the springs 60 together with the spring 39 force the upper body section 42 upwardly relative to the piston assembly and the jaws 33 outwardly to release the specimen 13.

The forces from the wedging action which tend to separate the cam surfaces 47,47 of the upper body section 42 are resisted by the cap screws 50 and the reaction of forces against the shoulder surface formed by the annular flange 44.

Because the outer grip housing 20 is relatively massive and the cap screws 50 can be preloaded, there will be no movement of the upper body section 42 separating the surfaces 47,47 under normal loading conditions. There is a constant preload, or constant clamping force on the specimen 13 so that the specimen loading does not change during testing. The load path of the clamping force is from the pressurized hydraulic fluid in the chamber 69 to the lower body section 21, through the cap screws 50 to the upper body section 42 and then to the grip jaws 33. The specimen 13 as shown is a sheet metal specimen, and thus relatively lightweight. Of course, the jaws 33 of the grip 14 can be adapted (or replaced) for acceptance of other types of specimens 13, such as cylindrically ended specimens.

If the grip jaws 33 are to be removed, the cap screws 50 are taken out, and the upper body portion 42 removed from the lower body section 21. This permits the springs 60 to be moved out of the T-slot 31 because dowel 61 will be removed with the upper body section 42, and the jaws 33 then can be slid out of the end of the T-slot 31 formed in the grip jaw mounting body assembly 23.

Therefore, if the jaw surfaces wear or if different jaws are to be placed into the grip assembly, this can be done relatively quickly and easily.

When the grip is reassembled, the cap screws 50 are again tightened down to provide a sufficient preload for the amount of load that is to be exerted by the grip jaws 33.

A FURTHER EMBODIMENT-FIGS. 6 AND 7

Figures 6, 7:
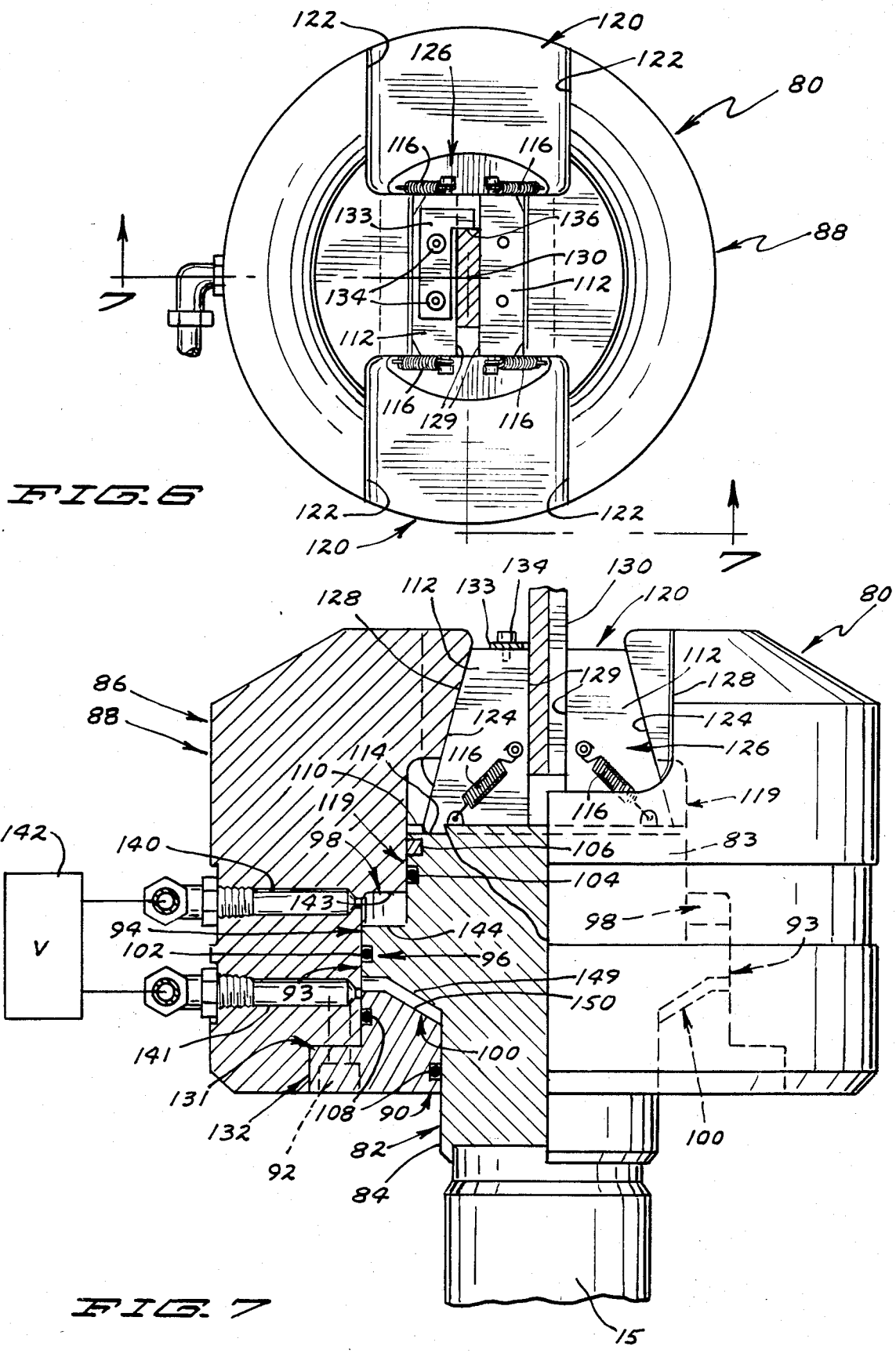
FIG. 6 is a top plan view of another embodiment of the grip of the present invention, with a specimen clamped therein shown in section.
FIG. 7 is a sectional view taken as on line 7—7 in FIG. 6.

A second embodiment of the side loading specimen grip of the present invention is shown in FIGS. 6 and 7. In this embodiment, the specimen grip 80 is mounted to a load frame in a manner similar to that of the specimen grip 14 described above. The general function and structure of the specimen grip 80 shown in FIGS. 6 and 7 is same or similar to the specimen grip illustrated in FIGS. 1-5 and the above discussion is equally applicable to grip 80 in most instances.

Grip 80 has a main mounting body 82 which has an upper piston portion 83 and a lower neck portion 84. The neck portion 84 is attached to the load frame in a conventional manner, such as being secured to an actuator rod 15. Thus, as the actuator (such as actuator 12 shown in FIG. 1) is operated to extend or retract its actuator rod 15, the main mounting body 82 moves with it.

Mounted concentrically about the main mounting body 82 is an outer grip housing 86 of the specimen grip 80. The housing 86 is comprised of an upper housing section 88 and a lower housing section 90, which are fixedly secured together by suitable fastening means such as a plurality of cap screws 92. The upper housing section 88 has a bore 93 defined therein into which the lower housing section 90 extends, and when so connected, the upper and lower housing sections form an internal annular recess 94. The main mounting body 82 has an outer annular dividing rim 96 which extends into the annular recess 94 to divide it into an upper chamber 98 and a lower chamber 100. The combination of the main mounting body 82 and the outer grip housing 86 as described above and shown in FIG. 7 thus forms a double acting hydraulic cylinder arrangement.

Hydraulic fluid introduced into the upper chamber 98 causes the outer grip housing 86 to move upwardly with respect to the main mounting body 82, while the introduction of hydraulic fluid in the lower chamber 100 causes the outer grip housing 86 to move downwardly with respect to the main mounting body 82. As the hydraulic fluid in one chamber is pressurized, the hydraulic fluid in the other chamber is depressurized to permit the relative movement described above. Sealing means, such as an O-ring 102 about the dividing rim 96 prevents hydraulic fluid from leaking from one chamber to the other. The upper chamber 98 is sealed from upwardly leakage of hydraulic fluid by similar sealing means, such as an O-ring 104, and a wiper 106 is used if desired. The lower chamber 100 is sealed from downward leakage of hydraulic fluid by sealing means such as O-rings 108.

The upper end of the main mounting body 82 has a transverse horizontal slot 110 defined therein. A pair of hardened grip jaws 112 are provided, each having its bottom end formed to be received in and slidable laterally along the slot 110. As shown, a floor 114 of the slot 110 forms an upper hardened surface along which the grip jaws 112 slide when the specimen grip 80 is actuated. The group jaws 112 are each provided with bias means, such as springs 116 which urge the grip jaws 112 apart or tend to separate the two grip jaws 112. The springs 116 also urge the grip jaws 112 downwardly into engagement with the floor 114 of the slide 110. One end of each spring 115 is secured to a side of its respective grip jaw 112, while the other end thereof is secured to the upper end (piston portion 83) of the main mounting body 82 to place the spring 116 in tension. Thus, when the main mounting body 82 moves longitudinally along the test axis, the grip jaws 112 move simultaneously with it.

The upper housing section 88 has a bore indicated at 119 above the bore 93 in which the upper end (piston portion 83) of the main mounting body 82 can move. Furthermore, when the specimen grip 80 is actuated, there is clearance between an upper surface of the main mounting body 82 and an upper end of the bore 119, as shown in FIG. 7.

As can be seen in FIG. 6, the upper housing section 88 has a pair of cut aways or recesses 120 on opposite sides thereof and thus is generally symmetrical. Each recess 120 forms a pair of surfaces 122 on the upper housing section 88 that are substantially vertical surfaces. Surfaces 122 are on opposite sides of a pair of cam surfaces 124, 124 that are formed on an internal cavity 126 of the upper housing section 88. The cam surfaces 124 are formed to engage outer wedge surfaces 128 on the grip jaws 112. The internal cavity 126, which extends to the top or upper end of the upper housing section 88, is thus laterally open on both ends through the recesses 120. Each grip jaw 112 has a substantially vertical inner grip surface 129 facing said inner grip surface on the other grip jaw of the pair, as shown in FIG. 7. The space between the inner grip surfaces 129 of the grip jaws 112, which defines the opening in which a specimen 130 can be inserted, is accessible from either side of the specimen grip 80 through the recesses 120. The recesses 120 therefore provide direct access from the sides into the grip jaws 112 and permits the lateral insertion of a specimen 130 between the jaws 112 when the jaws 112 are separated or loosened. There is thus no need to move the entire specimen grip 80 longitudinally in order to install the specimen 130.

The cap screws indicated at 92 secure the upper and lower housing sections 88 and 90 together. These screws can provide a substantial pre-load of the upper housing section 88 against the lower body section 90, and thus keeps the housing sections 88 and 90. In addition, the cap screws 92 are mounted in an annular shoulder 131 of the lower housing section 90 which fits inside an annular recess 132 in the upper housing section 88. The upper housing section 88 is thus concentrically secured fits securely in place with respect to the lower housing section 90 as the annular shoulder 131 sits in the annular recess 132, and the cap screws 92 keep the housing sections 88 and 90 from separating when the specimen grip 80 is actuated.

If desired, an adjustable specimen stop 133 can be mounted on an upper end of one of the grip jaws 112. Specimen stop 133 is held in place by suitable fastening means, such as a pair of cap screws 134, 134. As shown in FIG. 6, the stop 133 has an edge 136 against which the specimen 130 can be placed to align the specimen 130 along the longitudinal test axis.

ACTUATION

Where the specimen 130 is to be inserted in the specimen grips 80, pressurized hydraulic fluid is introduced into the upper chamber 98 in order to move the upper housing section 88 upwardly relative to the main mounting body 82. This hydraulic pressure acts between the surfaces 143 and 144 to force the upper housing section 88 upwardly relative to the main mounting body 82. This permits the grip jaws 112 to separate, being pulled apart by the force of the springs 116. As shown in FIG. 7, suitable conduits 140 and 141 (also shown partially schematically) connect the the upper and lower chambers 98 and 100, respectively, to a valve 142 (shown schematically).

When pressurized hydraulic fluid is introduced into the upper chamber 98, pressurized fluid must be exhausted from the lower chamber 100 in order to permit movement of the outer grip housing 86 with respect to the main mounting body 82. Actuation of the valve 142 thus introduces hydraulic fluid under pressure into one chamber while exhausting such fluid from the other chamber simultaneously.

Once the specimen 130 has been slid in between the jaw gripping surfaces indicated at 148 in FIGS. 6 and 7, the valve 142 is actuated to introduce hydraulic pressure into the lower chamber 100 and exhaust such pressurized fluid from the upper chamber 98. This hydraulic pressure differential acts between the surfaces 149 and 150 to force the lower housing section 90 downwardly relative to the main mounting body 82. The cap screws 92 thus carry the upper housing section 88 downwardly as well. In turn, the cam surfaces 124 act on the outer wedge surfaces 128 of the grip jaws 112 to tend to move the grip jaws 112 horizontally toward each other. The grip jaws 112 slide on the floor 114 of the slot 110 in the main mounting body 82 and move only horizontally so that relative axial movement between the specimen 130 and the specimen grip 80 is virtually eliminated. During the clamping of the specimen 130, the main mounting body 82 (mounted on the actuator rod 15) does not move longitudinally, and thus the grip jaws 112 mounted thereon do not move as well (except horizontally toward each other).

By using a high enough hydraulic pressure, the gripping action (the clamping force of the grip jaws 112) becomes sufficiently high to preload the specimen grips 80 to a point where there is virtually no change in grip force nor relative movement between the grip jaws 112 and the cam surfaces 124 when the actuator is operated for testing the specimen 130. The grip jaws 112 are pre-loaded to a point where the tension load on the actuator rod 15 is less than the force being exerted by the hydraulic fluid under pressure in the lower chamber 100. The load path from the actuator rod 15 for both tensile and compressive specimen testing is thus through the main mounting body 82 and grip jaws 112 to the specimen 130.

In addition, by employing a straight horizontal jaw movement, which also is defined as a movement perpendicular to the longitudinal axis of the specimen, the specimen stresses are minimized during the initial gripping action. The use of a symmetrical outer grip housing 86 (as viewed in FIG. 6) to present uniform cam surfaces 124 and clamping motion to the grip jaws 112 eliminates lateral distortion of the gripping force on the specimen exerted by the grip 80 across the inner grip surfaces 129 of the grip jaws 112. There is no lateral gripping force differential on the specimen 30 as viewed from top to bottom in FIG. 6. Therefore, there is virtually no axial movement of the specimen during gripping nor any undesired bending moment applied to the specimen during gripping or testing.

When the specimen 130 has been tested, either to compressive or tensile failure or the like, and the parts are to be removed from the grips 80, the valve 142 is actuated to introduce pressurized hydraulic fluid into the upper chamber 98 and exhaust such pressurized fluid from the lower chamber 100. This forces the outer grip housing 86 upwardly relative to the main mounting body 82 which permits the grip jaws 112 to separate horizontally. The springs 116 urge the grip jaws 112 apart to release the specimen 130.

Because the outer grip body housing 86 is relatively unitary (except for the small lower housing section 90 at its lower end) and because it is relatively massive, there will be no movement tending to separate the cam surfaces 124 under normal loading conditions. There is a constant pre-load, or constant clamping force on the specimen 130 so that the specimen loading or clamping force does not change during testing. The load path of the clamping force is from the pressured hydraulic fluid in lower chamber 100 to the lower housing section 90, through the cap screws 92 to the upper housing section 88 and then to the grip jaws 112. The specimen 130 as shown is a sheet metal specimen, and thus relatively light weight. Of course, the group jaws 112 of the specimen grip 80 can be adapted (or replaced) for acceptance of other types of specimens 130, such as cylindrically ended specimens.

The grip jaws 112 are easily and quickly removable from the specimen grip 80 for replacement or repair. To remove the grip jaws 112, the valve 142 is actuated to pressurize the upper chamber 98 (and depressurize the lower chamber 100) to move the outer grip housing 86 upwardly with respect to the main mounting body 82. The identical recesses 120 are of size to permit lateral removal and insertion of the grip jaws 112 once the springs 116 are disconnected. The new or repaired grip jaw 112 is slid through the recess 120 so that its outer wedge surface 128 is aligned with the respective cam surface 124 of the upper housing section 88, the springs 116 are connected between the grip jaw 112 and the main mounting body 82, and the grip 80 is then ready for operation.

The side loading specimen grip as described above thus provides a more efficient and accurate grip for testing purposes. The grip is safer to operate than other grips since no longitudinal movement is required during specimen installation (where such movement could result in the catching or crushing of an operators hand or fingers). An operator need merely actuate the valve 142 to separate the grip jaws 112, slide a specimen 130 therebetween, center the specimen along the longitudinal test axis and actuate valve 142 to move the grip jaws 112 together to secure the specimen 130 in the grip 80. This simple loading and unloading operation of specimens not only makes the specimen testing system safer, but results in a faster system leading to higher production capabilities as well. The improved safety and operational system characteristics of the specimen grip of the present invention are further enhanced by the elimination of uneven lateral clamping forces exerted by the grip on the specimen during clamping and testing and the resulting elimination of any bending moment exerted by the grip on the specimen during load testing. Such potential bending moments are eliminated because of the symmetry of the housing portion of the grip which uniformly transmits the clamping force to and through the wedge jaws to the specimen.

The terms "upper" and "lower" have been used in the description, but as clearly can be seen in FIG. 1 the grips 14 (and grips 80) may be inverted. Thus these designations are for relative orientation only.

Although the present invention has been described with reference to preferred embodiments, workers skilled in the art will recognize that changes may be made in form and detail without departing from the spirit and scope of the invention.

What is claimed is:

1. A side loading specimen grip assembly suitable for use in both tensile and compressive loading of a specimen comprises a main mounting body, said main mounting body being adapted to be loaded by an actuator in direction along a longitudinal axis, means on said main mounting body defining a slide on an upper surface thereof, jaw means mounted on said slide for movement transverse to the longitudinal axis, said jaw means comprising a pair of opposed grip jaws mounted on said slide for simultaneous longitudinal movement therewith when the mounting body is loaded by the actuator, the grip jaws being movable toward and away from each other and having wedge surfaces thereon, a housing mounted on said main mounting body and having cam surfaces mating with said wedge surfaces so that upon movement of the housing relative to the mounting body along said longitudinal axis in a first direction the cam surfaces force said jaws to move toward each other, and cooperating cylinder and piston means between said main mounting body and said housing forming a chamber into which hydraulic fluid under pressure may be introduced to force the housing in direction along the longitudinal axis to tend to force the cam surfaces against the wedge surfaces and force the grip jaws together, said housing having a first recess so that the side portions of said grip jaws are accessible from the exterior of said housing and above the mounting body to permit installation and removal of a specimen from a side of the grip jaws and specimen grip assembly without the need for longitudinal movement of the grip jaws.

2. The grip assembly of claim 1 wherein said housing comprises two sections, a lower section formed in combination with the mounting body to define the hydraulic cylinder means, and an upper section having the cam surfaces defined therein, the first recess being on said upper section and opening to said cam surfaces laterally of said longitudinal axis to permit access to said grip jaws, and said upper section being longitudinally immovably secured to said lower section.

3. The grip assembly of claim 2 wherein said upper section is mounted on said lower section with a plurality of preloaded cap screws.

4. The grip assembly of claim 3 wherein cooperating pilot shoulder means is provided between the upper and lower sections of the housing tending to prevent separation of the housing radially outward from the center longitudinal axis thereof.

5. The grip assembly of claim 1 wherein said slide comprises the upper surface of said main mounting body, said upper surface having a slot defined therein extending transverse to said longitudinal axis across said main mounting body, said slot comprising a T-shaped slot formed by overhanging shoulders on which the grip jaws slide, said grip jaws having a tang portion extending into said slot.

6. The grip assembly of claim 1 and further comprising an adjustable specimen stop for alignment of the specimen relative to the longitudinal axis.

7. The grip assembly of claim 1 wherein the upper section of the housing has a second recess identical with and opposite from the first recess so that the housing is symmetrical in configuration about the longitudinal axis.

8. A side loading specimen grip assembly suitable for use in both tensile and compressive loading of a specimen comprises a main mounting body having a neck and an enlarged upper piston portion, means on said neck adapted to be attached to an actuator for movement of said main mounting body in direction along its longitudinal axis, a pair of grip jaws mounted for movement longitudinally simultaneously with the mounting body, the grip jaws being mounted on the end of said piston portion opposite from the neck and for movement transversely to the longitudinal axis, said grip jaws being generally centered along said longitudinal axis and movable transversely toward and away therefrom, and having side surfaces on opposite sides of a plane defined by said longitudinal axis and a line extending in the direction of movement of said grip jaws, said grip jaws having outwardly and upwardly facing wedge surfaces, a housing member, said housing member including a first portion having a bore therethrough which surrounds said neck and said piston portion, and forms a pressure tight chamber with respect to said piston portion on a side of said piston portion such that pressure in said chamber tends to move said housing in direction along the longitudinal axis, said housing having a second section partially surrounding said grip jaws including a pair of cam surfaces adapted to mate with the wedge surfaces of said grip jaws, movement of said housing when pressure is in said chamber causing said cam surfaces to engage the grip jaws and urge the grip jaws toward each other, said second section of said housing having a recess on one side therefore open to said cam surface so that substantially the entire sides of both of the grip jaws are accessible from the exterior of said outer housing, and said outer housing surrounding the rest of the portions of said grip jaws and the housing recess permitting insertion and removal of specimens laterally from the space between the grip jaws when the grip jaws are separated without the need for longitudinal movement of the grip jaws to facilitate specimen installation and removal.

9. A symmetrical side loading specimen grip assembly suitable for use in both tensile and compressive loading of a specimen comprises:
a main mounting body, said main mounting body being adapted to be loaded by an actuator in direction along a longitudinal axis;
means on said main mounting body defining a slide on an upper surface thereof;
jaw means mounted on said slide for movement transverse to the longitudinal axis, said jaw means comprising a pair of opposed grip jaws that are movable toward and away from each other and the axis and having wedge surfaces thereon;
a housing mounted on said main mounting body about the axis and having cam surfaces mating with said wedge surfaces so that upon movement of the housing relative to the mounting body along said longitudinal axis in a first direction the cam surfaces force said jaws to move simultaneously toward the axis and each other;
cooperating cylinder and piston means between said main mounting body and said housing forming a first annular chamber extending concentrically about the axis into which hydraulic fluid under pressure may be introduced to force the housing in a first direction along the longitudinal axis to tend to force the cam surfaces against the wedge surfaces and force the grip jaws uniformly together; and
said housing being generally symmetrical and having a pair of opposed identical recesses therein so that the side portions of said grip jaws are accessible from opposite sides of the exterior of said housing and above the mounting body.

10. The grip assembly of claim 9 wherein the cooperating cylinder and piston means forms a second annular chamber extending concentrically about the axis and sealably spaced axially from the first annular chamber and into which hydraulic fluid under pressure may be introduced to force the housing in a second, opposite direction along the longitudinal axis.

11. The grip assembly of claim 10, and further comprising:
means for selectively supplying hydraulic fluid under pressure to one of the annular chambers while exhausting such fluid from the other annular chamber.

12. A symmetrical side loading specimen grip assembly suitable for use in both tensile and compressive loading of a specimen along a longitudinal test axis comprises:
a main mounting body having a neck and an upper piston portion, means on said neck adapted to be attached to an actuator for movement of said main mounting body in direction along the longitudinal axis;
a pair of grip jaws mounted for movement on the end of said piston portion opposite from the neck and for movement transversely to the axis, said grip jaws being centered along said longitudinal axis and movable transversely toward and away therefrom, and having side surfaces on opposite sides of a plane defined by said longitudinal axis and a line extending in the direction of movement of said grip jaws, said grip jaws having outwardly and upwardly facing wedge surfaces;
a housing, said housing including first and second sections which combine to concentrically surround said neck and form a pressure tight chamber with respect to said main mounting body on a side of said piston portion such that pressure in said chamber tends to move said housing in direction along the longitudinal axis, the second section of the housing partially surrounding said grip jaws and including a pair of cam surfaces adapted to mate with the wedge surfaces of said grip jaws, movement of said housing when pressure is in said chamber causing said cam surfaces to engage the grip jaws and urge the grip jaws simultaneously toward the longitudinal axis and each other; and said second portion of said housing having a pair of opposed identical recesses open to said cam surfaces so that substantially the entire sides of both of the grip jaws are accessible from opposite sides of the exterior of said outer housing, and said outer housing surrounding the rest of the portions of said grip jaws and the housing recesses permitting insertion and removal of specimens laterally from the space between the grip jaws when the grip jaws are separated.

* * * * *